United States Patent

Tanaka et al.

[11] Patent Number: 5,142,091
[45] Date of Patent: Aug. 25, 1992

[54] α, β-UNSATURATED KETONES AND KETOXIME DERIVATIVES

[75] Inventors: Motoaki Tanaka, Tokorozawa; Yu-ichi Hagiwara, Iruma; Makoto Kajitani, Saitama; Mitsugi Yasumoto, Honjo, all of Japan

[73] Assignee: Taiho Pharmaceutical Company Limited, Tokyo, Japan

[21] Appl. No.: 690,939

[22] PCT Filed: Nov. 19, 1990

[86] PCT No.: PCT/JP90/01512
§ 371 Date: Jul. 10, 1991
§ 102(e) Date: Jul. 10, 1991

[87] PCT Pub. No.: WO91/07374
PCT Pub. Date: May 30, 1991

[30] Foreign Application Priority Data
Nov. 21, 1989 [JP] Japan ............................... 1-303900

[51] Int. Cl.⁵ .................. C07C 255/37; C07C 255/40; C07C 255/62
[52] U.S. Cl. .................... 558/405; 558/408; 560/35; 560/51; 560/53
[58] Field of Search .................. 558/405, 408; 560/35, 560/51, 53

[56] References Cited
FOREIGN PATENT DOCUMENTS
63-130564 6/1988 Japan .

OTHER PUBLICATIONS
C.A. Tanaka et al 115: 183271z (1991).
C.A. Tanaka et al 115: 158717t (1991).
C.A. Buggle et al 76: 59293v (1971).
C.A. Jan.-Jun. 1972–Formula Index, p. 1145f.

Primary Examiner—Joseph Paul Brust
Attorney, Agent, or Firm—Nikaido, Marmelstein, Murray & Oram

[57] ABSTRACT

The present invention provides an α, β-unsaturated ketone and ketoxime derivative represented by the formula

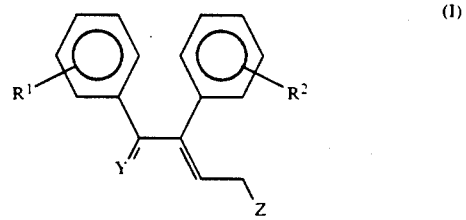

(I)

wherein Y is oxygen atom or hydroxyimino group, Z is cyano or alkoxycarbonyl group, $R^1$ and $R^2$ are the same or different and are each hydrogen atom or lower alkoxyl group.

The α, β-unsaturated ketones and ketoxime derivatives of the invention are useful as an intermediate for preparing a (3,4-diarylisoxazol-5-yl)acetic acid derivatives which is useful as an anti-inflammatory agent, analgesic and antipyretic.

3 Claims, No Drawings

α, β-UNSATURATED KETONES AND KETOXIME DERIVATIVES

TECHNICAL FIELD

The present invention relates to α,β-unsaturated ketone and ketoxime derivatives which are novel compounds. The present compounds are useful as intermediates for preparing (3,4-diarylisoxazol-5-yl)acetic acid derivatives which are represented by the formula

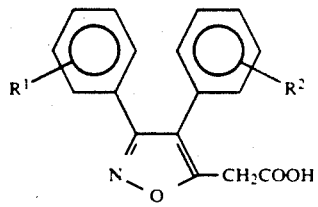

(A)

wherein $R^1$ and $R^2$ are the same or different and are each a hydrogen atom or lower alkoxyl, and which are useful as anti-inflammatory agents, analgesics and antipyretics.

BACKGROUND ART

JF-A-59764/1981 discloses (3,4-diarylisoxazol-5-yl)acetic acid derivatives as a compound having anti-inflammatory, analgesic and antipyretic activities. The processes thereof are known in (1) the above publication and (2) JP-A-75471/1985.

JP-A-59764/1981

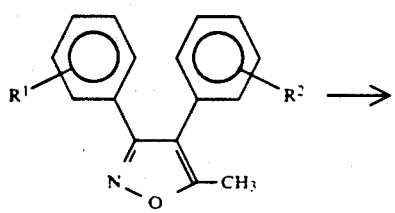

-continued

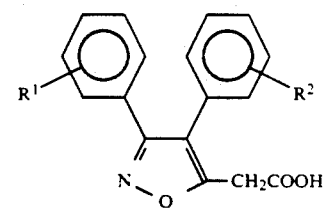

wherein $R^1$ and $R^2$ are as defined above.

The above contemplated compound is obtained by reacting 3,4-diaryl-5-methylisoxazole with n-butyl lithium in tetrahydrofuran while cooling by use of dry ice-acetone mixture, pouring the reaction mixture into pulverized dry ice, and then treating the mixture with acid.

JP-A-75471/1985

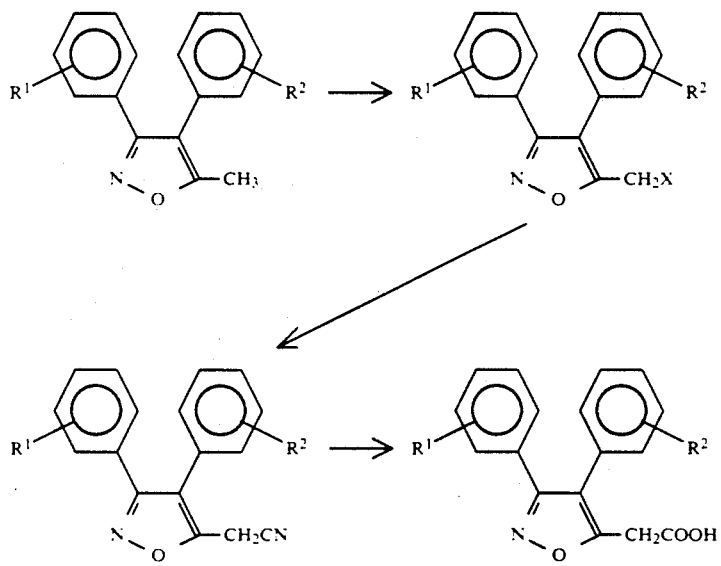

wherein X is halogen atom, $R^1$ and $R^2$ are as defined above. This process comprises reacting 3,4-diaryl-5-methylisoxazole with a halogenating agent and then with a cyanogenation agent to obtain 3,4-diaryl-5-cyanomethylisoxazole, and subjecting the same to solvolysis.

The present inventors have investigated an industrial process for preparing (3,4-diarylisoxazol-5-yl)acetic acid derivatives and found the methods disclosed in (1) and (2) have various problems. In the method (1), the reagent, n-butyl lithium, is liable to ignite and causes problems in fire and safety when used in a large quantity. Further, this method comprises problems in process efficiency including operation efficiency, because dry ice having high hygroscopicity is used in the reaction which requires anhydrous reaction condition and low temperature −70°C. The method (2) is more complicate than the method (1), and is not a preferable industrial process in view of safety due to the use of cyano compound.

An object of the present invention is to provide novel α,β-unsaturated ketone and ketoxime derivatives useful as intermediates for preparing the compound (A) by a simple process which uses no dangerous reagent and is excellent in safety and operation efficiency.

DISCLOSURE OF THE INVENTION

The present invention provides an α,β-unsaturated ketone and ketoxime derivative represented by the formula

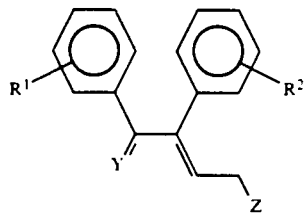

(I)

wherein Y is oxygen atom or hydroxyimino group, Z is cyano or alkoxycarbonyl group, $R^1$ and $R^2$ are the same or different and are each hydrogen atom or lower alkoxyl group.

In the present invention, examples of alkoxycarbonyl groups represented by Z are straight-chain or branched-chain alkoxycarbonyl groups having 2 to 7 carbon atoms, such as methoxycarbonyl, ethoxycarbonyl, n-propoxycarbonyl, isopropoxycarbonyl, n-butoxycarbonyl, isobutoxycarbonyl, secbutoxycarbonyl, tert-butoxycarbonyl, pentyloxycarbonyl and hexyloxycarbonyl. Examples of lower alkoxyl groups represented by $R^1$ and $R^2$ are straight-chain or branched-chain lower alkoxyl groups having 1 to 6 carbon atoms, such as methoxy, ethoxy, n-propoxy, isopropoxy, n-butoxy, isobutoxy, secbutoxy, tert-butoxy, pentyloxy and hexyloxy. The present α,β-unsaturated ketone and ketoxime derivatives are useful as intermediates for preparing (3,4-diarylisoxazol-5-yl)acetic acid derivatives which are useful as anti-inflammatory agents, analgesics and antipyretics and which are represented by the formula

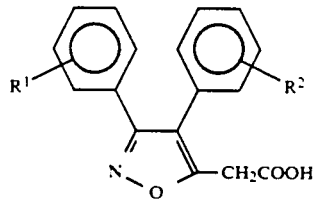

(A)

wherein $R^1$ and $R^2$ are the same or different and are each a hydrogen atom or lower alkoxyl group.

The compound (I) in the present invention is prepared, for example, in accordance with the following reaction scheme.

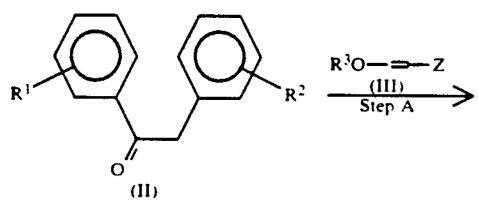

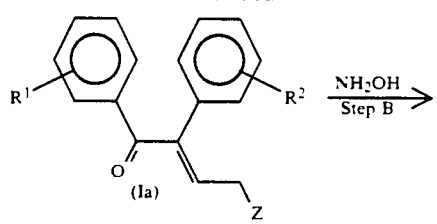

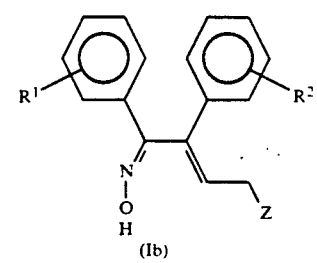

wherein Z, $R^1$ and $R^2$ are as defined above, and $R^3$ is lower alkyl group.

Examples of lower alkyl groups represented by $R^3$ in the above scheme are straight-chain or branched-chain alkyl groups having 1 to 6 carbon atoms, such as methyl, ethyl, n-propyl, isopropyl, n-butyl, sec-butyl, tert-butyl, pentyl and hexyl.

More specifically, the steps represented by the above reaction scheme are performed in the following manner.

Step A

A deoxybenzoin derivative represented by the formula (II) is reacted with an alkoxyacrylonitrile or alkoxyacrylic acid derivative represented by the formula (III) in a suitable solvent in the presence of a base to obtain a desired compound of the formula (I a). The solvent is not limited specifically insofar as it does not participate in the reaction. Examples of useful solvents are various organic solvents including methanol, ethanol, tert-butanol and like alcohols, tetrahydrofuran, dioxane and like ethers, benzene, toluene, xylene and like aromatic hydrocarbons, carbon tetrachloride, dichloroethane and like hydrocarbon halides, pyridine, dimethylformamide, etc. These solvents can be used singly or in admixture. Examples of useful bases are sodium hydroxide, sodium hydride, sodium amide, sodium methoxide, potassium tert-butoxide, sodium tert-butoxide, butyl lithium and like alkali bases, triethylamine, diethylaminopyridine and like organic bases, etc. For the reaction, it is desirable to use 1 to 3 moles of the compound of the formula (III) per mole of the compound of the formula (II), and 0.1 to 3 moles of the base per mole of the compound of the formula (II). The reaction is conducted at a temperature of up to 200°C., preferably from 0° C. approximately to the boiling point of the solvent. The reaction usually takes about 0.5 to about 20 hours for completion.

Step B

The compound represented by the formula (I a) and obtained by step A is reacted with hydroxylamine or a salt thereof in a suitable solvent to thereby obtain a desired compound represented by the formula (I b). The salt of hydroxylamine to be used for the reaction is not limited specifically and is, for example, the commercially available hydrochloric acid salt, sulfuric acid salt or the like. The solvent is not limited specifically insofar as it does not participate in the reaction. Examples of useful solvents are various organic solvents including methanol, ethanol, isopropanol and like alcohols, tetrahydrofuran, dioxane and like ethers, dimethylformamide, etc. These solvents can be used singly or in admixture, or in the form of a mixture thereof with water. For the reaction, it is desirable to use 1 to 10 moles of hydroxylamine or a salt thereof per mole of the compound of the formula (I a). The reaction is conducted at a temperature of 0° to 200° C., preferably from 40° C. approximately to the boiling point of the solvent. The completion of the reaction usually takes about 1 to about 30 hours. Further, it is possible as required to add an acid or base to the reaction system, or to conduct the reaction in a solvent mixture with a buffer solution, etc.

The compound of the invention thus obtained can be isolated and purified by usual known methods, for example, by distillation, recrystallization or silica gel column chromatography.

In the present invention, $\alpha,\beta$-unsaturated ketone and ketoxime derivatives of the formula (I) include isomers due to the double bond, and both isomers are included in the present invention.

The ketoxime compound represented by the formula (I b) and prepared by the above process is subjected, as isolated or as it is without isolation, to cyclization with use of a halogenating agent in a suitable solvent to obtain (3,4-diarylisoxazol-5-yl)acetate derivative or (3,4-diarylisoxazol-5-yl)acetonitrile derivative, and further the derivative is subjected to solvolysis or to hydrolysis in the presence of an acid or base, whereby a (3,4-diarylisoxazol-5-yl)acetic acid derivative represented by the formula (A) and having anti-inflammatory and analgesic activities can be derived from the compound of the invention. The halogenating agent is not limited specifically and is, for example, chlorine, bromine, iodine, N-chlorosuccinimide, N-bromosuccinimide, or the like. The solvent is not limited specifically insofar as it does not participate in the reaction. Examples of useful solvents are dichloromethane, chloroform, carbon tetrachloride and like hydrocarbon halides, benzene, toluene and like aromatic hydrocarbons, methanol, ethanol and like alcohols, diethyl ether, tetrahydrofuran and like ethers, acetone, hexane, etc. In the above cyclization, it is preferable to use 1 to 3 moles of the halogenating agent per mole of the ketoxime compound of the formula (I b). The reaction is conducted at a temperature of $-70°$ to 150° C., preferably from $-20°$ C. approximately to the boiling point of the solvent. The solvolysis or hydrolysis can be conducted by solvolysis process disclosed in JP-A-75471/1985 or by the hydrolysis process generally employed in the art concerned. Generally used as the acid is an inorganic acid such as hydrochloric acid, sulfuric acid or nitric acid, or as the base is an inorganic base such as sodium hydroxide, potassium hydroxide or sodium carbonate. The latermentioned Reference Example shows the detail of synthesis of (3,4-diarylisoxazol-5-yl)acetic acid derivative from the compound of the present invention.

Best mode of carrying out the invention

The present invention will be described below in detail with reference to examples and reference examples.

EXAMPLE 1

Preparation of methyl 4,5-bis(4-methoxyphenyl)-5-oxo-3-pentenoate

To 430 ml of tert-butanol were added 128 g of deoxyanisoin, 67.3 g of potassium tert-butoxide and 116 g of methyl 3-methoxyacrylate, and the mixture was stirred at 70° C. for 3 hours. After the completion of reaction, the reaction mixture was allowed to stand at room temperature with addition of n-hexane. The product separating out was filtered off and the residue was dried at a reduced pressure, giving 175 g (yield 92%) of potassium salt of the above-identified compound as a yellow solid.

IR absorption spectrum (KBr): $\nu$max(cm$^{-1}$) 1734, 1664, 1604.

NMR spectrum (pyridine-d$_5$) $\delta$(ppm) 3.58(3 H, s), 3.60(3 H, s), 3.66(3 H, s), 5.65(1 H, d), 6.83(2 H, d), 6.94(2 H, d), 7.64(2 H, d), 7.81(2 H, d), 9.01(1 H, d).

The above potassium salt was dissolved with 1000 ml of ethyl acetate and 300 ml of 3N sulfuric acid. The organic layer was collected, washed with 3N sulfuric acid and a saturated aqueous solution of sodium chloride, and dried over anhydrous sodium sulfate. The organic layer was concentrated at a reduced pressure, giving 153 g (yield 90%) of the above-identified compound as an oily product.

An NMR spectrum revealed that the compound was a mixture of isomers (about 6:4) due to a double bond. The mixture was recrystallized from hexane-ethyl acetate as required, whereby one of the isomers was isolated in the form of white crystals.

Melting point 101°~103° C.

IR absorption spectrum (KBr): $\nu$max(cm$^{-1}$) 1732, 1640, 1600.

NMR spectrum (CDCl$_3$) $\delta$(ppm): 3.31(2 H, d), 3.72(3 H, s), 3.80(3 H, s), 3.85(3 H, s), 6.37(1 H, t), 6.90(4 H, d), 7.23(2 H, d), 7.89(2 H, d).

The mother liquor further gave the other isomer of the compound in the form of an oily product.

IR absorption spectrum (KBr): $\nu$max(cm$^{-1}$) 1732, 1662, 1596.

NMR spectrum (CDCl$_3$) $\delta$(ppm) 3.15(2 H, d), 3.65(3 H, s), 3.77(3 H, s), 3.83(3 H, s), 6.30(1 H, t), 6.6~7.1(4 H, m), 7.30(2 H, d), 7.92(2 H, d).

EXAMPLE 2

Preparation of 4,5-bis(4-methoxyphenyl)-5-oxo-3-pentenenitrile

The identified compound was obtained as an oily product by conducting the same reaction as in Example 1 with the exception of using 3-methoxyacrylonitrile instead methyl of 3-methoxyacrylate.

IR absorption spectrum (NaCl): $\nu$max(cm$^{-1}$) 2250, 1660, 1606.

NMR spectrum (CDCl$_3$) $\delta$(ppm): 3.17(2 H, d), 3.78(3 H, s), 3.85(3 H, s), 6.03(3 H, t), 6.7~7.0(4 H, m), 7.27(2 H, d), 7.90(2 H, d).

EXAMPLE 3

Preparation of methyl 5-hydroxyimino-4,5-bis(4-methoxyphenyl)-3-pentenoate

A 24.5 g quantity of methyl 4,5-bis(4-methoxyphenyl)-5-oxo-3-pentenoate obtained in Example 1 and 51.5 g of hydroxylamine hydrochloride was refluxed with heating in a mixture of 650 ml of methanol and 72 ml of water for 23 hours. With the progress of reaction at this time, 0.9 equivalent weight of sodium hydrogentarbonate was added in divided portions to the reaction system. On completion of the reaction, the methanol was distilled off at a reduced pressure. The residue was dissolved with water and ethyl acetate, and the organic layer was collected, washed with a saturated aqueous solution of sodium chloride and dried over anhydrous magnesium sulfate. The organic layer was concentrated at a reduced pressure, and the residue was subjected to silica gel column chromatography (eluants: ethyl acetate-n-hexane) for separation and purification, affording 23 g (yield 90%) of the above-identified compound as an oily product.

IR absorption spectrum (NaCl) νmax(cm⁻¹) 1732, 1608.

NMR spectrum (CDCl₃) δ(ppm): 3.09~3.20(2 H, m), 3.65(3 H, s), 3.76(3 H, s), 3.77(3 H, s), 6.48(1 H, t), 6.81(4 H, d), 7.35(2 H, d), 7.58(4 H, d), 8.72(1 H, bs).

EXAMPLE 4

Preparation of 5-hydroxyimino-4,5-bis(4-methoxyphenyl)-3-pentenenitrile

The identified compound was prepared as an oily product by conducting the same reaction with hydroxylamine hydrochloride as in Example 3 with the exception of using 4,5-bis(4-methoxyphenyl)-5-oxo-3-pentenenitrile in place of methyl 4,5-bis(4-methoxyphenyl)-5-oxo-3-pentenoate.

IR spectrum (NaCl):
νmax(cm⁻¹) 2252, 1596.

NMR spectrum (CDCl₃) δ(ppm): 3.12, 3.15(2 H, dd), 3.77(3 H, s), 3.78(3 H, s), 6.18(1 H, t), 6.84(4 H, d), 7.32(2 H, d), 7.55(2 H, d), 8.46(1 H, bs).

Reference Example 1

Preparation of methyl (3,4-bis(4-methoxyphenyl)-isoxazol-5-yl]acetate

In 50 g of benzene was dissolved 3.05 g of methyl 5-hydroxyimino-4,5-bis(4-methoxyphenyl-3-pentenoate obtained in Example 3. Thereto was added gradually 3.91 g of N-bromosuccinimide at room temperature and the mixture was stirred at the same temperature for 2 hours. After completion of the reaction, ethyl acetate was added to the reaction mixture for dilution, and the organic layer was washed with an aqueous solution of potassium carbonate and then with a saturated aqueous solution of sodium chloride and dried over anhydrous magnesium sulfate. The organic layer was concentrated at a reduced pressure, and the residue was subjected to silica gel column chromatography (eluants: ethyl acetate-n-hexane) and crystallized from ether, giving the above-identified compound.

Melting point 67°~68° C.

IR absorption spectrum (KBr) νmax(cm⁻¹) 1730.

NMR spectrum (CDCl₃) δ(ppm): 3.73(3 H, s), 3.77(2 H, s), 3.79(3 H, s), 3.82(3 H, s), 6.83(2 H, d), 6.90(2 H, d), 7.15(2 H, d), 7.40(2 H, d).

Reference Example 2

Preparation of [3,4-bis(4-methoxyphenyl)isoxazol-5-yl]acetic acid

To 15 ml of 2% aqueous solution of sodium hydroxide was added 1.77 g of methyl [3,4-bis(4-methoxyphenyl)isoxazol-5-yl]acetate obtained in Reference Example 1 and the mixture was stirred at 40° C. over night. After completion of the reaction, the reaction mixture was washed with ether twice, and thereto was added 5 ml of 10% HCl while cooling with ice. The mixture was extracted with ethyl acetate, and the organic layer was washed with a saturated aqueous solution of sodium chloride and dried over anhydrous magnesium sulfate. The organic layer was concentrated at a reduced pressure, giving the above-identified compound as white solid.

Melting point 147°~148° C.

IR absorption spectrum (KBr): νmax(cm⁻¹) 1728.

NMR spectrum (CDCl₃) δ(ppm): 3.79(3 H, s), 3.81(2 H, s), 3.83(2 H, s), 6.82(2 H, d), 6.92(2 H, d), 7.15(2 H, d), 7.40(2 H, d), 10.10(1 H, bs).

Industrial applicability

The α,β-unsaturated ketones and ketoxime derivatives of the invention are useful as an intermediate for preparing a (3,4-diarylisoxazol-5-yl)acetic acid derivative which is useful as an anti-inflammatory agent, analgesic and antipyretic and which is represented by the formula

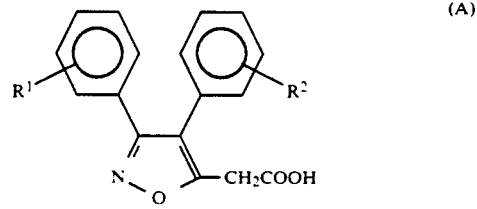

(A)

wherein R¹ and R² are the same or different and are each a hydrogen atom or lower alkoxyl group.

We claim:

1. An α,β-unsaturated ketone and ketoxime derivative represented by the formula

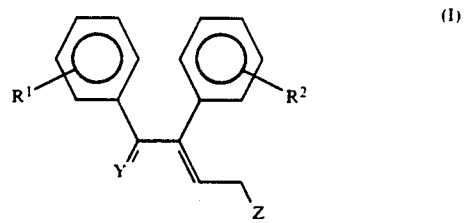

(I)

wherein Y is an oxygen atom or a hydroxyimino group, Z is a cyano or an alkoxycarbonyl group, and R¹ and R² are the same or different and are each a hydrogen atom or lower alkoxyl group; provided, however that when Z is an alkoxycarbonyl group, then R¹ and R² are the same or different and are each a lower alkoxyl group.

2. An α,β-unsaturated ketone and ketoxime derivative represented by the formula

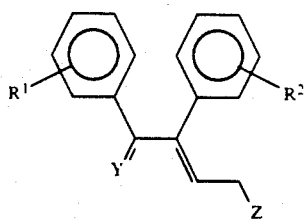

(I)

wherein Y is an oxygen atom or a hydroxyimino group, Z is a cyano or an alkoxycarbonyl group, and $R^1$ and $R^2$ are the same or different and are each a lower alkoxyl group.

3. An α,β-unsaturated ketone and ketoxime derivative represented by the formula

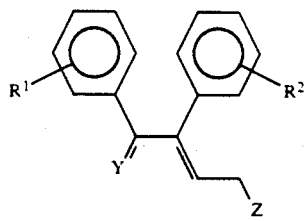

(I)

wherein Y is an oxygen atom or a hydroxyimino group, Z is a cyano group and $R^1$ and $R^2$ are the same or different and are each a hydrogen atom or lower alkoxyl group.

* * * * *